US00PP11605P

United States Patent [19]

Pieters

[11] Patent Number: Plant 11,605

[45] Date of Patent: Oct. 31, 2000

[54] CHRYSANTHEMUM PLANT NAMED 'GEDI RA8'

[76] Inventor: Dirk Pieters, Schierveldestraat 3A, Oosnieuwkerke, 8840 Staden, Belgium

[21] Appl. No.: 09/168,915

[22] Filed: Oct. 8, 1998

[51] Int. Cl.[7] ..... A01H 5/00

[52] U.S. Cl. ..... Plt./298

[58] Field of Search ..... Plt./298

*Primary Examiner*—Howard J. Locker

*Attorney, Agent, or Firm*—Christie, Parker & Hale, LLP

[57] ABSTRACT

A new plant variety of chrysanthemum producing red daisy-type flowers.

1 Drawing Sheet

BACKGROUND OF THE INVENTION

The present invention is directed to a new and distinct variety of chrysanthemum botanically classified as *Dendranthema morifolium*. The varietal denomination of the new chrysanthemum is 'GEDI RA8'.

The new variety was discovered as natural whole plant mutation in a controlled planting of the variety 'Alcala' (U.S. Plant Pat. No. 10,211) in Staden, Belgium. The new variety has been asexually reproduced by vegetative cuttings in Ventura County, Calif. and the distinguishing characteristics are retained through successive generations of asexual reproduction.

SUMMARY OF THE INVENTION

'GEDI RA8' produces red, daisy-type non-brittle, herbaceous flowers on a mounding perennial plant suitable for garden decoration.

COMPARISON WITH PARENTS

'GEDI RA8' differs from its parent in having red ray florets whereas 'Alcala' ray florets are purple.

BRIEF DESCRIPTION OF ILLUSTRATION

The accompanying photograph shows a typical specimen of the plant and flowers of the new variety with colors being as nearly true as possible with illustrations of this type.

DESCRIPTION OF THE PLANT

The following description of the new variety is of specimens grown in a greenhouse in Ventura County, Calif. in the month of July. 'GEDI RA8' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting. It has been observed that longevity of individual blooms of 'GEDI RA8' is about 17 days and the response time is about 6.5 weeks. No growth retardant is used on the plants described. Useful growing conditions include night temperatures of about 62°–65° F. and day temperatures of about 70°–75° F. The variety is naturally blooming mid to late September in California.

Plant:

*Habit.*—Non-brittle, mounding herbaceous perennial.

*Height.*—About 16 cm.

*Number of breaks from pinch.*—About 7–8.

*Length of lateral branches.*—About 14 cm.

*Stem color.*—Near 138B.

Foliage:

*Leaf arrangement.*—Alternate.

*Number of leaves per lateral branch.*—About 12 fully expanded leaves.

*Leaf size.*—Length: About 4.2 cm. width: About 2.1 cm.

*Leaf shape.*—Ovate.

*Attachment.*—Petioled.

*Leaf apex.*—Acute.

*Base.*—Tapered.

*Margin.*—Palmately lobed.

*Aspect.*—Slightly undulating.

*Surface.*—Top: Lightly pubescent. Bottom: Lightly pubescent.

*Venation color.*—Upperside: Near 137C. Underside: Near 144A.

Petiole:

*Length.*—About 1 cm.

*Color.*—Near 137B.

Color:

*Mature leaf.*—Top: Near 137A. Bottom: Near 137C.

*Young leaf.*—Top: Near 137B. Bottom: Near 138B.

Bloom:

*Inflorescence form.*—Cyme.

*Bloom type.*—Daisy.

*Number of blooms per branch.*—About 12.

*Diameter of fully expanded bloom.*—About 4.5 cm.

*Depth of fully expanded bloom.*—About 1.2 cm.

*Diameter of disc.*—About 1.3 cm.

*Sepal number.*—About 30. Color: Near 137B.

*Peduncle.*—Length: Peduncle length is shortest at the terminal flower and progressively longer moving down the stem, the longest peduncle length is on average about 6.5 cm, the shortest peduncle length is on average 3.1 cm. Surface: Pubescent. Color: Near 138A.

*Flower Bud* (*when just showing color*).—Color: Near 46B. Diameter: Near 0.7 cm. Height: About 1 cm. Shape: Oblong.

Ray florets:

*Number per inflorescence.*—About 30.

*Texture.*—Matte.

*Shape.*—Oblanceolate.

*Apex.*—Obtuse.

*Base.*—Tapered.

*Margin.*—Entire.

*Aspect.*—Slightly recurved.

*Length.*—About 2.1 cm.
*Width.*—About 0.4 cm.

Disc florets:
*Number per inflorescence.*—About 100.
*Texture.*—Glossy.
*Shape.*—Cylindric.
*Margin.*—Entire.
*Length.*—About 0.4 cm.
*Width.*—About 0.08 cm.

Fragrance: Moderate.

FLOWER COLOR

General inflorescence description: Red daisy with a yellow/orange disc.

Ray florets, top side:
*Immature.*—Near 45A.
*Mature.*—Near 45B.
*Fading.*—Near 44B.

Ray floret, under side:
*Immature.*—Near 45C.
*Mature.*—Near 45B.
*Fading.*—Near 44B.

Disc florets:
*Immature.*—Near 5B.
*Mature.*—Near 21B.
*Fading.*—Near 20A.

Changes as the flower ages: Daisy form becomes very open and abundant pollen is released. Flower color fades slightly, more orange/red tones apparent.

Reproductive organs:
*Ray florets.*—Pistillate. Stigma shape: 2 branched. Stigma color: Near 2B. Style length: About 0.2 cm. Style color: Near 1D.
*Disc florets.*—Stigma shape: Linear. Stigma color: Near 2B. Style Length: About 0.2 cm. Style color: Near 154D. Stamen number: About 5. Anther length: About 0.2 cm. Pollen color: Near 15A. Pollen quantity: Abundant.

What is claimed is:

1. A new and distinct chrysanthemum plant of the variety substantially as herein shown and described.

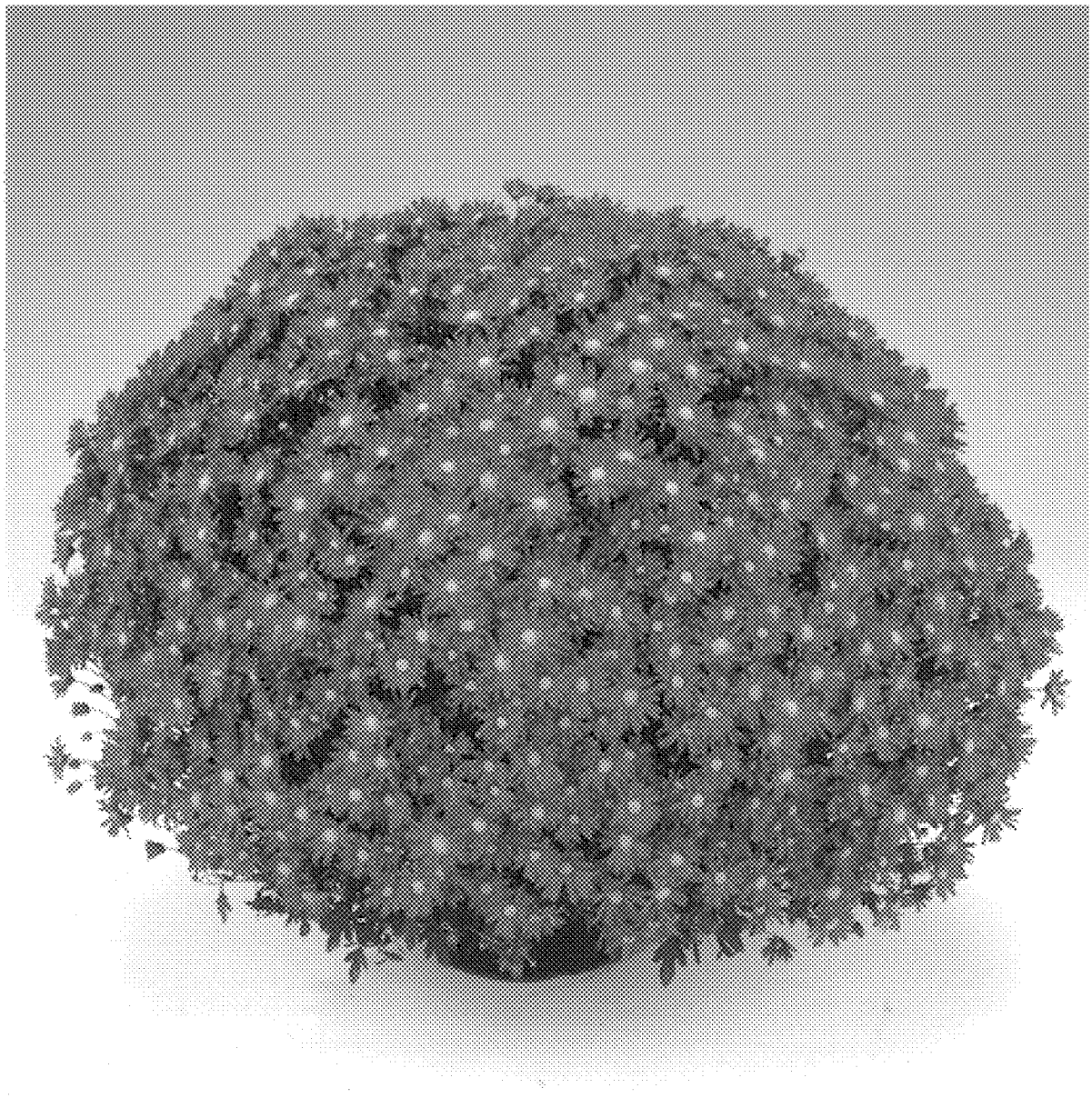

* * * * *